United States Patent [19]

Couderc et al.

[11] 4,294,717
[45] Oct. 13, 1981

[54] COMPOSITIONS CONTAINING AN ALKALI METAL MONO- OR POLYALKYLARYLSULFONATE AND THE CORRESPONDING HYDROPEROXIDE, PROCESS FOR THEIR PREPARATION AND DETERGENT COMPOSITIONS CONTAINING THEM

[75] Inventors: Pierre Couderc; Jean-Luc Grardel, both of Bethune; Gérard Caux, Bully les Mines, all of France

[73] Assignee: Societe Chimique des Charbonnages SA, Paris, France

[21] Appl. No.: 30,666

[22] Filed: Apr. 16, 1979

[30] Foreign Application Priority Data

Apr. 14, 1978 [FR] France ................................. 78 11082
Oct. 10, 1978 [FR] France ................................. 78 28907

[51] Int. Cl.$^3$ ........................ C11D 7/54; C11D 7/56; C11D 9/42
[52] U.S. Cl. ........................................ 252/97; 252/96; 252/98; 252/99; 252/102; 252/135; 252/186; 260/502 R
[58] Field of Search ...................... 252/95, 96, 97, 99, 252/186, 135, 530, 549, 431 C, 98, 102; 260/502 R, 505 R; 568/569, 570, 573, 574, 575, 576, 577

[56] References Cited

U.S. PATENT DOCUMENTS

| | | | |
|---|---|---|---|
| 2,632,026 | 3/1953 | Conner | 568/573 |
| 2,664,447 | 12/1953 | Lorand et al. | 568/575 X |
| 2,664,448 | 12/1953 | Lorand et al. | 568/575 |
| 2,715,646 | 8/1955 | Hawkins et al. | 568/573 |
| 2,829,158 | 4/1958 | Weldy | 260/502 R |
| 3,583,924 | 6/1971 | Demangeon | 252/102 |
| 3,746,646 | 7/1973 | Boixader | 252/95 |
| 3,753,915 | 8/1973 | Demangeon | 252/95 |

FOREIGN PATENT DOCUMENTS

| | | | |
|---|---|---|---|
| 38-13626 | 7/1963 | Japan | 568/569 |
| 356272 | 11/1972 | U.S.S.R. | 568/569 |

Primary Examiner—P. E. Willis, Jr.
Attorney, Agent, or Firm—Millen & White

[57] ABSTRACT

A solid, dry composition is provided, comprising (a) an alkali metal alkylarylsulfonate and (b) the corresponding hydroperoxide obtained by hydroperoxidation of the alkali metal alkylarylsulfonate. A process for producing the composition, and detergents containing the composition as a bleaching agent are also provided.

36 Claims, 1 Drawing Figure

COMPOSITIONS CONTAINING AN ALKALI METAL MONO- OR POLYALKYLARYLSULFONATE AND THE CORRESPONDING HYDROPEROXIDE, PROCESS FOR THEIR PREPARATION AND DETERGENT COMPOSITIONS CONTAINING THEM

BACKGROUND OF THE INVENTION

The present invention relates to solid compositions comprising an alkali metal mono- or polyalkylarylsulfonate and the corresponding hydroperoxide; it also relates to an improved process for the preparation of mixtures of alkali metal mono- or polyalkylarylsulfonate and the corresponding hydroperoxide and a process for the preparation of said mixtures in dry state; it also relates to the use of the hydroperoxide as bleaching agent and to water soluble detergent compositions containing the solid compositions comprising an alkali metal mono- or polyalkylarylsulfonate and the corresponding hydroperoxide.

The synthesis of alkali metal arylsulfonate compounds with a ROOH hydroperoxide function on the aryl nucleus has been little studied. U.S. Pat. No. 2,829,158 describes a process for the preparation of compounds of this type and of mixtures, in aqueous solution, of alkylarylsulfonate hydroperoxide and alkylarylsulfonate. This patent teaches that one could possibly prepare the pure hydroperoxide starting from the thus prepared aqueous solutions, by evaporatng the solvent of said hydroperoxide at a very low temperature, for example lower than $-10°$ C., but no specific example is disclosed.

It would be of interest to have an industrial process allowing the preparation, in dry state, of mixtures of alkali metal mono- or polyalkylarylsulfonates and the corresponding hydroperoxides, said dry mixtures being used in detergent compositions as disclosed hereunder or as initiators of radical reactions.

DETAILED DISCUSSION

The present invention has at its first object a process for the preparation of aqueous solutions of alkali metal mono- or polyalkylarylsulfonates containing the corresponding hydroperoxides in suitable quantities, by action of oxygen on an alkali metal mono- or polyalkylarylsulfonate according to which oxygen is reacted at a temperature not higher than 85° C. with an aqueous solution of an alkali metal alkylarylsulfonate, said solution having a pH comprised between 9 and 10.5, in the presence of 1–50 ppm of cobalt, as cobalt naphthenate, with respect to the alkali metal alkylarylsulfonate present.

The alkali metal mono- or polyalkylarylsulfonates used as starting materials in the process of the invention are compounds having the formula:

wherein
M is an alkali metal, preferably sodium
RH is an alkyl radical, preferably isopropyl
R' is a lower alkyl radical, preferably a methyl, ethyl, n-propyl or isopropyl radical
n is an integer equal to 0, 1, 2, 3, or 4 and preferably equal to 0 or 1.

The hydroperoxides obtained according to the process of the invention have the formula:

Their structure is demonstrated by Carbon 13 NMR. For example, the chemical shift of the central carbon is the isopropyl radical—$CH(CH_3)_2$ which is about 34 ppm for the hydrocarbon compound is 83 ppm for the hydroperoxide and 72 ppm for the alcohol formed by decomposition of the hydroperoxide, which thus has the formula:

In the aforementioned specific example of sodium isopropylbenzenesulfonate (sodium cumenesulfonate), the corresponding hydroperoxide and alcohol have the following structures, respectively, The preparation of alkali metal hydroperoxides of mono- or polyalkylarylsulfonates in aqueous medium by action of oxygen (as pure oxygen, as air or as air enriched in oxygen) is greatly improved if one uses cobalt naphthenate as catalyst. It has been found that by using said catalyst, the peroxidation could be performed at a temperature of 80°–85° C. as compared to 90°–95° C. without catalyst. And this is all the more important as, at temperatures higher than 85° C., the decomposition of the hydroperoxide even in basic medium is not to be neglected. The presence of cobalt naphthenate allows a better use of the oxygen in this reaction and a less important formation of alcohol arising from the decomposition of the hydroperoxide. But too large amounts of cobalt naphthenate should be avoided. It has been found that when used in amounts higher than 50 ppm (expressed as cobalt) with respect to the starting sulfonate, the naphtenate catalysed the hydroperoxide decomposition. Thus the optimal amount of cobalt naphthenate is comprised between 1 and 50 ppm cobalt by weight with respect to the starting sulfonate.

The peroxidation reaction is performed in slightly basic medium, and preferably at a pH value comprised between 9 and 10.5. It has indeed been found that at higher and lower pH values, the decomposition of hydroperoxide into alcohol is not to be neglected.

The pressure of peroxides and specially of hydrogen peroxide promotes the start of the peroxidation and an amount of 10—20 parts by weight of hydrogen peroxide, at 50% by weight, for 100 parts by weight of starting sulfonate, gives good results.

When operating the peroxidation at a temperature of 80° C., at a pH value of 10, in the presence of less than 10 ppm cobalt as cobalt naphtenate with respect to the starting mono- or polyalkylarylsulfonate, and deliberately limiting to a rather low value the conversion rate of the sulfonate, a reaction mixture is obtained which, once dried under vacuum at 20° C., gives a powder which contains about 85–90% unreacted sulfonate, 10–15% of the corresponding hydroperoxide and in which no alcohol, resulting from the decomposition of the hydroperoxide, could be detected. It is possible to obtain a powder with a higher quantity of hydroperoxide by submitting the reaction mixture to a fractional crystallization, such as described below and by repeating if necessary this operation on the filtrate.

It has been found that in order to obtain compounds which are interesting from an industrial point of view, it is advised to perform the peroxidation reaction until a dry sample obtained by vacuum drying an aliquot of the aqueous solution contains at least about 25%, by weight, of hydroperoxide. On the other hand, said peroxidation should not be performed beyond a total transformation rate of the sulfonate of about 50%, in order to avoid too large a decomposition of the hydroperoxide into alcohol. Such a decomposition indeed lowers the selectivity of the peroxidation reaction of the starting sulfonate, thus the yield of hydroperoxide with respect to the amount of oxygen absorbed. This yield is higher than or equal to 75% for a total conversion rate of the starting sulfonate not exceeding 50%.

The sodium sulfonates used as starting material are prepared by know methods by reacting concentrated sulfuric acid at elevated temperature on the corresponding hydrocarbon compound, neutralising with sodium hydroxide, cooling, filtering and drying of the precipitate.

The peroxidations of sodium mono- or polyalkylarylsulfonates thus obtained are performed in a heated tubular reactor, operating in closed circuit with recycling of the gaseous phase into which a gaseous oxygen current is injected. The absorption of oxygen versus time follows a S-shaped curve with relatively short induction periods. The rate of gaseous phase, which flows as continuous recycle through the reaction mass, is of about 80–90 liters/hour.

The amount of hydroperoxide in the reaction mixture and the dry products is measured by chemical analysis (iodometry).

The amount of alcohol from the hydroperoxide decomposition is measured by proton NMR ($CH_3$ adjacent to the carbon which has the OH function).

A further object of the present invention is a new composition of matter comprising a solid and dry mixture of an alkali metal mono- or polyalkylarylsulfonate and its hydroperoxide, said composition being substantially stable at room temperature.

This mixture can in addition contain a small amount of the alcohol formed by decomposition of the hydroperoxide.

More precisely, such compositions can contain, by weight:
 5 to 75% of an alkali metal mono- or polyalkylarylsulfonate
 25 to 70% of the hydroperoxide of said mono- or polyalkylarylsulfonate
 0 to 30% of the alcohol from the decomposition of said hydroperoxide.

Such dry compositions can be obtained by simple evaporation, to dryness, of the solution obtained by the hereabove described process, but due to the fact that very high peroxide yields cannot be obtained by the peroxidation reaction, it will in practice be difficult to obtain dry products with a reasonably high amount of peroxide.

It has been found that an industrial preparation of the hereabove defined dry compositions can be performed by treating the reaction mixture obtained at the end of the peroxidation reaction so as to promote a partial crystallization of said mixture, filtering the thus obtained suspension and evaporating the filtrate to dryness at a maximum temperature of 40° C., under vacuum. It has indeed been found that the alkylarylsulfonate used as starting material is less soluble, in water or lower alcohols, than the corresponding hydroperoxide. Such fractional crystallization can be repeated if desired on the filtrate after, for example, partial evaporation of the water.

In order to perform this partial crystallization, one of the following means can be used: cooling of the reaction mixture between 0° and 20° C. or concentration at 40° C. under vacuum and cooling between 0° and 20° C. It is also possible to dry concentrate the reaction mixture (and use directly the dried mixture obtained, for appropriate applications), take it up with methanol, cool the suspension to about 5° C. and filter the precipitate. The filtrate, which is enriched in hydroperoxide, is then concentrated to dryness at a maximum temperature of 40° C., under vacuum.

In their application as components of detergent compositions, the dry solid mixtures of alkali metal mono- or polyalkylarylsulfonates and of the corresponding hydroperoxides can replace at least partly the sodium perborate or equivalent products which in known detergent compositions, are used as bleaching agent.

Powder detergents usually used in aqueous solution for the washing of textile fibers at elevated temperature generally contain mineral persalts as bleaching agents. Amongst these, one of the most frequently used is sodium perborate, which can represent up to 30% by weight of the washing powder.

In can be shown that in this application the hydroperoxide contained in the solid dry mixtures of the invention acts primarily as a bleaching agent; the other components of said mixtures are also probably beneficial especially in the minor properties of the detergents obtained (solftening properties, surface active properties).

Owing to the stability of the products contained in these mixtures, and especially of the hydroperoxide, detergents containing them are particularly suitable for washing at elevated temperatures (for example about 90° C.).

A further object of the present invention is detergent compositions containing a hydroperoxide of an alkali metal mono- or polyalkylarylsulfonate.

The preferred hydroperoxide is the hydroperoxide of sodium isopropylbenzenesulfonate (hydroperoxide of sodium cumenesulfonate).

Amongst the products containing the hydroperoxide, there will be advantageously used the stable mixtures containing 25 to 70% by weight of alkali metal alkylarylsulfonate hydroperoxide, 5 to 75% by weight of an alkali metal alkylarylsulfonate and up to 30% by weight of alcohol from the decomposition of said hydroperoxide. The alkali metal alkylarylsulfonate component is usually the same as the starting material for the preparation of said hydroperoxide.

These mixtures can replace an equal weight of sodium perborate in detergent compositions. Thus a detergent containing up to 30% by weight of said mixtures can be prepared. But, owing to the effectiveness of said mixtures as detergents and bleaching agents, it is generally advised to limit the amount of said mixtures in detergents to the value corresponding to 0.1–5% of hydroperoxide in the washing powder, by weight.

It is also possible to replace only partly the usual perborate by the mixtures of the invention; it is thus particularly advised to use simultaneously on the one hand the mixtures of the invention in amonts corresponding to 2–4% by weight hydroperoxide and on the other hand sodium perborate in amount of less than 5% by weight and preferably about 2%, with respect to the detergent composition.

Even with such low proportions of bleaching agent, the stains and soiling of the textile material completely disappear.

The effectiveness of a washing powder is determined by the degree of whiteness of a washed textile material. This whiteness degree is of the same magnitude, for a given active oxygen rate, for the detergent compositions of the invention which, moreover, contain little hydroperoxide, and for detergents with a low amount of perborate. It is substantially equivalent for the detergent compositions with low hydroperoxide content, and for known, detergent powders containing about 30% sodium perborate.

It is possible to improve the results obtained with the detergent compositions having a low hydroperoxide content by the addition of trace amounts of cupric salts (for example copper sulfate); the copper amount being lower than 1000 ppm, preferably comprised between 100 and 800 ppm, with respect to the detergent powder. This is quite surprising since the addition of trace amounts of cupric salts to a detergent powder containing perborate lowers the effectiveness of such powder. It is thus possible, with the compositions of the invention, to use without damage water containing trace amounts of copper salts, either by nature of the water or due to the use of copper pipes. However it has been found that the presence of copper salts is beneficial for some stains (particularly for Immedial black dyeing) but is detrimental if the textile to be washed has been stained with wine. In the latter case, it is possible to improve the whiteness degree of the washed textile by adding beforehand to the detergent powder a copper complexing agent. Among the known complexing agents for copper which can be advantageously used in this invention one may mention nitrilotriacetic acid (NTA) and/or one of its alkali metal salts and ethylenediaminetetracetic acid (EDTA) and/or one of its alkali metal salts or mixture of these various complexing agents; taking into account the amount of copper which can be used, there will generally be used 0.1–5% NTA, preferably 0.5–2% by weight and 0.1–2% EDTA by weight, with respect to the detergent powder.

The powder detergent compositions of the invention will thus contain:

the dry solid mixtures containing an alkali metal mono- or polyalkylarylsulfonate, the corresponding hydroperoxide and optionally the alcohol from the hydroperoxide decomposition.

if necessary the copper and complexing agents additives mentioned hereabove and, the known ingredients used in detergents such as one or more anionic detergents such as sodium dodecylbenzenesulfonate, one or more soaps such as sodium tallow soap, a non ionic detergent (polyoxyethylenated or polyoxypropylenated compound), sodium tripolyphosphate as sequestring agent and sodium silicate.

In addition said solid detergent compositions can also contain:

low amounts of a base, for example sodium hydroxide, in order that the solutions prepared from these powders have a suitable pH value (preferably comprised between 9 and 12).

sodium carbonate and/or sulfate used as builders and compounds such as optical brighteners, perfumes, and the like.

It has further been found that the use of the solid dry mixtures of the invention in detergent compositions permits a reduction or even elimination of the use, in said detergent compositions, of sodium dodecylbenzenesulfonate (or any equivalent compound) generally present in most detergent compositions. This reduction or elimination of the use of sodium dodecylbenzenesulfonate is possible particularly in detergent compositions in which the perborate has been partly or wholly replaced by the mixtures containing the hydroperoxide, the sulfonate and optionally the alcohol.

The detergent compositions of the invention moreover give rise to a surprising result: it has been found that they have a certain softening effect, which obviates the need to add a softening agent during the rinsing. This softening effect seems to be due to the alcohol which is present in the mixtures or which forms by decomposition of the hydroperoxide during the use of the detergent compositions.

There will now be described the general washing conditions and its effectiveness.

The detergent compositions are prepared by weighing the given amounts of the various ingredients then dissolving in water which has been demineralised then made hard up to a given degree of hardness by addition of calcium carbonate (generally 300 ppm of $CaCO_3$). For the washing there was used a laboratory apparatus, each bowl of said apparatus being charged with 6 g powder and 600 ml water. The pH value of the thus obtained solution was brought to the desired value by addition of trace amounts of sodium hydroxide; sodium hydroxide can also be incorporated in the powder during the powdering. Preferably the washing solution has a pH value comprised between 9 and 12 and still more preferably of $11\pm0.5$. In all the examples hereunder there will be given the pH of the detergent solution before washing; it being understood that the pH value falls by about 0.5 during the washing operation.

The solution was heated to 30° C. then kept 15 minutes at this temperature then the baskets containing the textile were put into the bowls and agitation was started. Temperature was raised from 30 to 90°-95° C. during 40 minutes then kept 50 minutes at 90°-95° C. The baskets were soaked in running water and the textile samples were rinsed with demineralised water then dried.

The washings were performed on test textile samples EMPA soiled with the following artificial stains: blood, red wine, Immedial black (sulfur black dye) which are called hereunder blood, wine and black.

Figure 1:
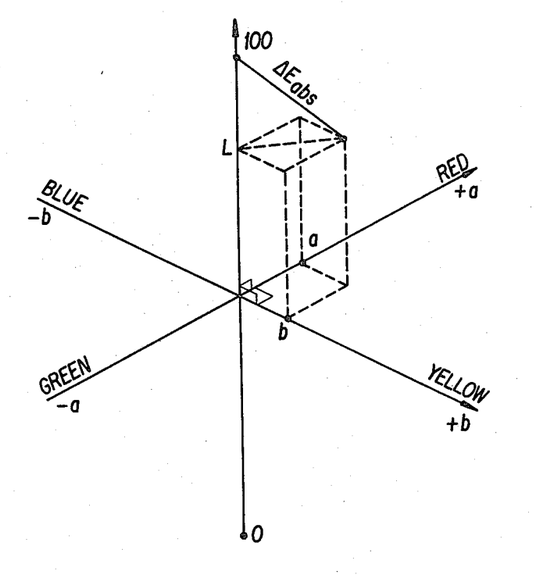
The drawing shows a schematic representation of the uniform chromaticity system for representing color variations.

The washing efficiency of a given detergent is measured by the uniform chromaticity system L, a, b "cube-root" (1958) which allows a representation of the color variations. In this system, schematically represented on the annexed drawing, "L" represents the "pure" whiteness degree (Luminance) between absolute black (0) and pure white (100); "a" is, according to its sign, a colour tending towards green (negative values) or towards red (positive values), and "b" a colour tending towards blue (negative values) or towards yellow (positive values). In this system with three perpendicular axes, the value obtained for a sample will be represented by a point. The distance from this point to another, representing the total chromaticity variation between both, in such that:

$$\Delta E = \sqrt{(L_1 - L_2)^2 + (a_1 - a_2)^2 + (b_1 - b_2)^2}$$

Taking as reference point $L_1$, $a_1$, $b_1$ (100,0,0) representing "pure" maximum theoretical whiteness, the absolute chromaticity variation for the measured sample (L, a, b) will be equal to:

$$\Delta E = \sqrt{(100 - L)^2 + a^2 + b^2}$$

the lower this value, the better the washing.

The values L, a and b are given directly by the measuring apparatus, a reflexion colorimeter.

The following examples will illustrate the invention in greater detail:

EXAMPLE 1

Peroxidation of sodium 2,4-diisopropylbenzenesulfonate 160 g sodium diisopropylbenzenesulfonate, 40 ppm (with respect to the sulfonate) cobalt as cobalt naphthenate at 6% cobalt, 480 g water, 20 g hydrogen peroxide at 49.7% by weight, and 3.1 g sodium carbonate to bring the pH value of the reaction medium to 9.5 were introduced in the reactor described hereabove. The gaseous phase was passed through the reaction mixture heated to 84° C. while admitting pure oxygen in said gaseous phase. The oxygen absorption rate, which was slow at the beginning, reached a value of about 0.5 g/hr after 4 hrs.

The weight amount of hydroperoxide in the reaction mixture was 6.2% after 10 hrs reaction (hydroperoxide yield based on oxygen: 88%).

The reaction proceeded a further 6 hrs. The hydroperoxide content of the reaction mixture was 7.5% by weight and the hydroperoxide yield based on oxygen was 76%. A total of 7.2 g oxygen was absorbed.

The evaporation to dryness under vacuum at a temperature of 40° C. at most of one part of the reaction mixture gave a dry product having the following composition:
- 59% unreacted sulfonate
- 30% hydroperoxide of sodium 2,4-diisopropylbenzenesulfonate
- 9% of the alcohol from the decomposition of the hydroperoxide (The remainder being sodium carbonate)

The total conversion rate of the sulfonate was 37%, and the conversion rate into hydroperoxide was 28%.

The rest of the reaction mixture was cooled to 2° C. and filtered. The precipitate and the filtrate were separately dried under vacuum. The powders thus obtained, in substantially equal amounts, had the following compositions in % by weight:

|  | Precipitate | Powder from filtrate drying |
| --- | --- | --- |
| Unreacted sulfonate | 71% | 51% |
| Hydroperoxide | 18% | 40% |
| Alcohol | 11% | 7% |

EXAMPLE 2

Peroxidation of the sodium salt of meta-cymene sulfonic acid (2-methyl-4-isopropylbenzenesulfonic).

112 g sodium salt of meta-cymene sulfonic acid, 30 ppm (with respect to the sulfonate) of cobalt as naphthenate containing 6% cobalt, 665 g water, 20 g hydrogen peroxide at 49.7% by weight and 3 g sodium carbonate to bring the pH value of the medium to 9.7 were introduced into the reactor. Temperature was raised to 84.5° C. while recycling the gaseous phase in which oxygen was introduced at an average rate of 0.36 g/hr.

After 9 hrs reaction, the hydroperoxide content of the reaction mixture was 1.9% by weight (hydroperoxide yield based on oxygen: 92%).

The reaction was stopped after 21 hrs. There were consumed 5.06 g oxygen. At this time, the hydroperoxide content of the reaction mixture was 4% by weight (hydroperoxide yield based on oxygen: 77%).

Part of the reaction mixture was dried under vacuum. The dried product obtained contained
- 63% unreacted sulfonate
- 27.5% corresponding hydroperoxide
- 8% alcohol from hydroperoxide decomposition.

The total conversion rate of the sulfonate was 33%; the conversion rate into hydroperoxide was 25.5%.

The rest of the reaction mass was cooled to 20° C. and filtered. The precipitate obtained and the filtrate were separately dried under vacuum at a temperature of 40° C. at most. The precipitate accounted for ⅓ in the total amount of dried products obtained.

The analysis of these dried products gave the following compositions (% by weight):

|  | Precipitate | Dry powder from filtrate |
| --- | --- | --- |
| Unreacted sulfonate | 86% | 50% |
| Hydroperoxide | 10% | 39% |
| Alcohol | 4% | 10% |

EXAMPLE 3

Peroxidation of the sodium salt of para-cymene sulfonic acid (2-methyl-5-isopropylbenzenesulfonic acid)

195 g of the sodium salt of para-cymene sulfonic acid, 17 ppm (with respect to the sulfonate) of cobalt as naphthenate with 6% cobalt, 565 g water, 20 g hydrogen peroxide at 49.7% by weight and 3 g sodium carbonate to bring the pH value of the medium to 9.7 were introduced in the reactor. The recycling of the gaseous phase through the reaction mass was started while the temperature was raised to 85° C. Oxygen was introduced into the gas flow at an average rate of 0.88 g/hr.

After 8 hrs reaction, the hydroperoxide content of the reaction mixture was 4.7% by weight (hydroperoxide yield based on oxygen; 93%).

The reaction was stopped after 16 hrs. The hydroperoxide content of the reaction mixture was 6.3% by weight. The total amount of oxygen absorbed was 7.4 g and the hydroperoxide yield based on oxygen was 79%.

Part of the reaction mixture was dried under vacuum, which gave a product having the following composition (% by weight)
Unreacted sulfonate: 67%
Hydroperoxide: 25%
Alcohol: 6%

The total conversion rate of the sulfonate was 28%, and the conversion rate into hydroperoxide was 22%.

The remaining part of the reaction mixture was cooled to 2° C. and filtered, then precipitate and filtrate were separately dried at 20° C. under vacuum. The powders were obtained in a weight ratio of $\frac{2}{3}$ for the precipate and $\frac{1}{3}$ for the filtrate.

The dried products obtained had the following compositions (% by weight).

|  | Precipitate | Powder from filtrate |
|---|---|---|
| Sulfonate | 79% | 45% |
| Hydroperoxide | 18% | 38% |
| Alcohol | 2% | 15% |

EXAMPLE 4

The peroxidation of a mixture of sodium salts of meta and para-cymene sulfonic acids.

There were introduced into the reactor
146 g sodium salt of meta-cymene sulfonic acid
79 g sodium salt of para-cymene sulfonic acid
30 ppm (with respect to the mixture of sulfonates) of cobalt as naphthenate at 6% cobalt
710 g water
20 g hydrogen peroxide at 49.7% and
3 g sodium carbonate to bring the pH value to 9.6

The gaseous phase was recycled through the reaction mixture which was heated to 85° C.; oxygen was introduced at an average rate of 0.84 g/hr.

After 14 hrs reaction, the hydroperoxide content of the reaction mixture was 7.8% by weight (yield base on oxygen 92%).

The reaction was stopped after 20 hrs. The hydroperoxide content of the reaction mixture was 9.5% by weight. 12.9 g oxygen were absorbed. The hydroperoxide yield was 84.5% based on oxygen.

Part of the reaction mixture was dried under vacuum at a maximum temperature of 40° C.
Its composition was the following (% by weight)
Unreacted sulfonate: 52%
Hydroperoxide: 39%
Alcohol: 7%

The total conversion rate of the mixture of sulfonates was 42% and the conversion rate into hydroperoxide was 36%.

The remaining part of the reaction mixture was freed under vacuum of 10% of the water present, cooled to 20° C. where it had the aspect of a gel and filtered at that temperature.

There was obtained a filtrate and a precipitate which were dried separately under vacuum. The dried products obtained (weight ratio 1/1) had the following compositions (% by weight).

|  | Precipitate | Powder from the filtrate |
|---|---|---|
| Sulfonate | 69% | 36% |
| Hydroperoxide | 27% | 52% |
| Alcohol | 3% | 11% |

EXAMPLE 5

Peroxidation of the sodium salt of cumene sulfonic acid (p-isopropylbenzenesulfonic acid).

There were introduced into the reactor 185 g of the sodium salt of cumene sulfonic acid, 10 ppm of cobalt (with respect to the sulfonate) as naphthenate at 6% cobalt, 500 g water, 18 g of the solid dry mixture of the hydroperoxide of the sodium salt of cumene sulfonic acid and of the sodium salt of cumene sulfonic acid, said mixture coming from a previous operation (precipitate obtained by dry concentration then taken up with methanol as described hereunder) and containing about 30% hydroperoxide then 0.5 g sodium carbonate to bring the pH value to 10. The recycling of the gaseous phase was started and the mixture heated to 85° C. Oxygen at an average rate of 1.2 g/hr was introduced into the gaseous phase.

After 10 Hrs reaction, the hydroperoxide content of the reaction mixture was 12% by weight, the yield based on oxygen was 90% (86% when taking into account the hydroperoxide initially introduced), and the total amount of oxygen absorbed was 12 g.

The reaction mixture was dry concentrated under vacuum at 40° C. maximum and there was obtained a powder with the following composition (% by weight):
Unreacted sulfonate: 48%
Hydroperoxide: 40%
Alcohol of decomposition: 11%

The total conversion rate of the sulfonate was 48%; the conversion rate into hydroperoxide was 36%.

One part by weight of this powder was mixed with 2 parts by weight of methanol and the mixture was stirred a few minutes at 40° C. It was then cooled at 5° C. and the precipitate was filtered. The precipitate and the filtrate were separately dried under vacuum at 20° C. There was thus obtained a precipitate with 30% by weight hydroperoxide and a powder (from the filtrate) with 50% by weight hydroperoxide.

The following are examples of use of the compositions of the invention containing a hydroperoxide of a sodium mono- or polyalkylarylsulfonate in the preparation of detergent compositions.

The soiled test textile material used in the examples hereunder have following initial L, a, b and $\Delta E_{abs}$ values:

TABLE I

|  | L | a | b | $\Delta E_{abs}$ |
|---|---|---|---|---|
| Blood | 45.1 | +15 | +7.1 | 57.4 |
| Wine | 71.7 | +9,5 | +6.9 | 30.6 |
| Black | 70.6 | −0,06 | −1.9 | 29.5 |

The following abbreviations will be used:

Sodium dodecylbenzenesulfonate (about 50% active material): DDBS
Sodium tallow soap: Soap
Non ionic detergent: DNI
Sodium tripolyphosphate: TPP
Sodium silicate (about 44% active material): SiS
Tetrahydrated sodium perborate ($NaBO_3 4H_2O$): PBS
Nitrilotriocetic acid: NTA
Sodium salt of ethylenediaminetetracetic acid: EDTA
Sodium sulfate: SNa

EXAMPLE 6

This was a comparative example of washing without bleaching agent. There was used, with the general washing conditions described above, a powder containing (% by weight)

DDBS: 10%
Soap: 7%
DNI: 6%
TPP: 40%
SiS: 10%
SNa: 27%

The washing solution (1 part powder for 100 parts water) had a pH value of 10, set by a small amount of sodium hydroxide.

Following results were obtained:

TABLE II

| | L | a | b | $\Delta E_{abs}$ |
|---|---|---|---|---|
| Blood | 87 | 0.6 | 7.7 | 15.1 |
| Wine | 88 | 2 | 6.9 | 14.0 |
| Black | 73.6 | −0.1 | −2.4 | 26.5 |

It is to be noted that without bleaching agent black is nearly unwashed whereas for blood and wine L increases (sharply for blood), the red component is notably reduced and the yellow component is nearly unchanged.

EXAMPLE 7

This was a comparative example of washing with a normal detergent containing sodium perborate.

There was used, for washing at pH value 10, the following powder (% by weight).

DDBS: 10%
Soap: 7%
DNI: 6%
TPP: 40%
SiS: 10%
EDTA: 1%
PBS: 26%

The following results were obtained:

TABLE III

| | L | a | b | $\Delta E_{abs}$ |
|---|---|---|---|---|
| Blood | 90.3 | −0.7 | 13.2 | 16.4 |
| Wine | 93.8 | −0.7 | 2.8 | 6.8 |
| Black | 81.8 | −1.2 | −0.9 | 18.3 |

As compared to the powder without perborate, there is a much better washing of wine, a better washing of black but a slightly lower washing of blood, with an increase of the yellow component. There has also been noticed some stiffening of the textile material after washing, in the case of blood.

Washing at pH 12 is better for black and much better for blood, as shown hereunder:

TABLE IV

| | L | a | b | $\Delta E_{abs}$ |
|---|---|---|---|---|
| Blood | 92.2 | −0.1 | 7.1 | 10.5 |
| Wine | 94.2 | −0.6 | 2.4 | 6.3 |
| Black | 83.3 | −1.2 | −0.9 | 16.8 |

There have been added to the detergent composition 100 ppm of copper as $CuSO_4 5H_2O$, which corresponds to 1 ppm $Cu^{++}$ in the washing solution. Washing at pH 12 gave following results:

TABLE V

| | L | a | b | $\Delta E_{abs}$ |
|---|---|---|---|---|
| Blood | 86.8 | 0.04 | 8.2 | 15.5 |
| Wine | 88.5 | 2.1 | 8.5 | 14.4 |
| Black | 79.7 | −0.7 | −0.8 | 20.3 |

There can be noted a detrimental effect of copper addition in detergent powders containing perborate even though they contain EDTA.

By lowering the perborate content, in order to have an active oxygen content equivalent to that of 5.3% pure hydroperoxide of the invention, slightly less good results were obtained as shown by Table VI. The washing powder contained:

DDBS: 10%
Soap: 7%
DNI: 6%
TPP: 40%
SiS: 10%
EDTA: 1%
PBS: 3.2%
SNa: 22.8%

TABLE VI
(washing at pH 10)

| | L | a | b | $\Delta E_{abs}$ |
|---|---|---|---|---|
| Blood | 88.9 | 0.9 | 13.9 | 17.8 |
| Wine | 92.8 | −0.4 | 3.8 | 8.1 |
| Black | 76.7 | −1 | −2 | 23.4 |

By removing EDTA from this formulation, the $\Delta E_{abs}$ was lowered by about 1 point in the three cases.

EXAMPLES 8 to 22

These examples show the results of washing with the detergent powders of the invention.

In all these examples, there was used as bleaching agent sodium cumene sulfonate hydroperoxide as a mixture with sodium cumene sulfonate and with the alcohol from hydroperoxide decomposition. This mixture, which was a dry powder, contained 50%, 40% and 10% respectively of each of these three components.

It is the amount of this mixture (called HPC) which is shown in table VII.

The washings were performed as described hereabove. The pH value of the mixture was set by incorporating finely ground sodium hydroxide in the detergent compositions.

The characteristics of these compositions are shown in table VII and the results appear in table VIII.

Example 22 has been performed by replacing the sodium sulfate of example 19 by an equal weight of sodium carbonate ($Na_2CO_3$).

The replacement of sodium perborate by an equivalent amount (same oxidizing power) of "mixture"

(HPC) improves particularly the washing of blood stains, the addition of copper sulfate improves moreover the washing of black and the addition of NTA still improves the washing of wine stains.

There can also be noticed the influence of pH on washing, especially in case of blood and black.

EXAMPLE 23

Sodium cumene sulfonate hydroperoxide was replaced as bleaching agent by sodium m-diisopropylbenzenesulfonate monohydroperoxide.

The product obtained by peroxidation of sodium m-diisopropylbenzene sulfonate contained, in % by weight:

Hydroperoxide: 40%
Unreacted starting material: 50%
Alcohol from hydroperoxide decomposition: 10%

This mixture (HPDP) was incorporated in a detergent powder which had following composition (% by weight)

DDBS: 10%
Soap: 7%
DNI: 6%
TPP: 40%
SiS: 10%
PBS: 2%
HPDP: 10.7%
NTA: 0.5%
SNa: 13.8%
Cu: 100 ppm (as $CuSO_4 5H_2O$)

This powder was dissolved in 100 times its weight water and the pH of the solution was adjusted at 12 by adding trace amounts of sodium hydroxide.

Washing was performed under the conditions already described. It gave the following results.

|  | L | a | b | $\Delta E_{abs}$ |
|---|---|---|---|---|
| Blood | 92.3 | −0.3 | 5.9 | 9.7 |
| Wine | 93 | −0.1 | 4.8 | 8.5 |
| Black | 81.2 | −0.5 | −1.4 | 18.8 |

TABLE VII

Solid detergent compositions used
component in % by weight

| Ex. | DDBS | SOAP | DNI | TPP | SiS | PBS | HPC | NTA | EDTA | SNa | $Cu^{++}$ in ppm | pH value of the washing medium |
|---|---|---|---|---|---|---|---|---|---|---|---|---|
| 8 | — | 7 | 6 | 40 | 10 | — | 26.5 | — | — | 10.5 | 400 | 11 |
| 9 | 10 | 7 | 6 | 40 | 10 | — | 10 | — | — | 17 | 0 | 10.5 |
| 10 | 10 | 7 | 6 | 40 | 10 | — | 10 | — | — | 17 | 0 | 11.5 |
| 11 | 10 | 7 | 6 | 40 | 10 | — | 10 | — | — | 17 | 100 | 11.5 |
| 12 | 10 | 7 | 6 | 40 | 10 | 2 | 4 | — | — | 21 | 0 | 10 |
| 13 | 10 | 7 | 6 | 40 | 10 | 2 | 4 | — | — | 21 | 400 | 10 |
| 14 | 10 | 7 | 6 | 40 | 10 | 2 | 4 | — | — | 21 | 100 | 11 |
| 15 | 10 | 7 | 6 | 40 | 10 | 2 | 4 | — | — | 21 | 100 | 12 |
| 16 | 10 | 7 | 6 | 40 | 10 | 2 | 4 | 3.9 | — | 17.1 | 200 | 12 |
| 17 | 10 | 7 | 6 | 40 | 10 | 2 | 4 | 0.5 | — | 20.5 | 100 | 11 |
| 18 | 10 | 7 | 6 | 40 | 10 | 2 | 4 | 1 | — | 20 | 100 | 12 |
| 19 | 10 | 7 | 6 | 40 | 10 | 2 | 8 | 0.5 | — | 16.5 | 100 | 11 |
| 20 | 10 | 7 | 6 | 40 | 10 | 2 | 8 | 0.5 | — | 16.5 | 100 | 12 |
| 21 | 10 | 7 | 6 | 40 | 10 | 2 | 4 | — | 1 | 20 | 800 | 10 |
| 22 | 10 | 7 | 6 | 40 | 10 | 2 | 8 | 0.5 | — | $NaCO_3$ 16.5 | 100 | 11 |

TABLE VIII

Results of the washings Stains

| | BLOOD | | | | WINE | | | | BLACK | | | |
|---|---|---|---|---|---|---|---|---|---|---|---|---|
| Ex. | L | a | b | $\Delta E_{abs}$ | L | a | b | $\Delta E_{abs}$ | L | a | b | $\Delta E_{abs}$ |
| 8 | not measured | | | | not measured | | | | 85.8 | −0.6 | 1.2 | 14.3 |
| 9 | 89.2 | 0.7 | 10.7 | 15.2 | 88.9 | 1.5 | 6.5 | 12.1 | 74.7 | 0.04 | −2.1 | 25.4 |
| 10 | 92 | −0.2 | 6.9 | 10.6 | 88 | 1.8 | 6.8 | 13.9 | 77 | −0.1 | −2 | 23.1 |
| 11 | 91.5 | −0.05 | 7.2 | 11.1 | not measured | | | | 84.5 | −0.3 | −0.1 | 15.5 |
| 12 | 89.8 | 0.5 | 11 | 15 | 93.6 | −0.34 | 3.6 | 7.3 | 75.8 | −0.6 | −2.2 | 24.3 |
| 13 | 87.2 | 0.5 | 7.7 | 14.9 | 87.5 | 2.5 | 8 | 15 | 77.5 | 0.5 | −1.4 | 22.5 |
| 14 | 89.6 | 0.3 | 7 | 12.5 | 87.6 | 2.6 | 7.7 | 14.8 | 78.5 | −0.4 | −1.2 | 21.5 |
| 15 | 90.7 | −0.2 | 6 | 11.1 | 87.5 | 2.5 | 7.3 | 14.7 | 82.9 | −0.7 | 0.2 | 17.1 |
| 16 | 90.1 | −0.04 | 7 | 12.1 | 93.8 | −0.4 | 3.3 | 7 | 78.8 | −0.8 | −1.7 | 21.3 |
| 17 | 90.3 | 0.2 | 8.3 | 12.8 | 93.8 | −0.4 | 3.5 | 7.1 | 78.9 | −0.7 | −1.7 | 21.3 |
| 18 | 91.2 | −0.1 | 6.3 | 10.8 | 93.7 | −0.4 | 3.8 | 7.4 | 81.6 | −0.8 | −0.7 | 18.4 |
| 19 | 92.5 | −0.3 | 6.6 | 10 | 93.8 | −0.4 | 3.3 | 7 | 79.7 | −0.7 | −1.6 | 20.4 |
| 20 | 92 | −0.3 | 6 | 10 | 93.1 | −0.2 | 4.7 | 8.3 | 84 | −0.9 | 0.4 | 16 |
| 21 | 90.2 | 0.25 | 9.1 | 13.4 | 92.7 | −0.03 | 4.6 | 8.6 | 76.7 | −0.8 | −1.9 | 23.4 |
| 22 | 92.9 | −0.3 | 6.3 | 9.5 | 93.4 | −0.3 | 3.4 | 7.4 | 80 | −0.8 | 1.5 | 20 |

What is claimed is:

1. A solid, dry composition suitable for use as a bleaching agent in detergents, comprising:
   (a) at least one alkali metal alkylarylsulfonate having the formula:

wherein:
M is an alkali metal;
R' is lower alkyl; and
n is 0, 1, 2, 3 or 4; and (b) the hydroperoxide obtained by hydroperoxidation of said at least one alkali metal alkylarylsulfonate and having the formula:

wherein M, R' and n are as defined above.

2. The composition of claim 1 which further comprises the alcohol resulting from the partial decomposition of said hydroperoxide and having the formula whrein M, R' and n are as defined in claim 1.

3. The composition of claim 2, wherein the amount of said alcohol is up to 30% by weight.

4. The composition of claim 2, comprising 5–75% by weight of said at least one alkali metal alkylarylsulfonate; 25–70% by weight of said hydroperoxide; and up to 30% by weight of said alcohol.

5. The composition of claim 4, wherein said at least one alkali metal alkylarylsulfonate is the sodium salt of p-cumene sulfonic acid, cymene sulfonic acid or diisopropylbenzene sulfonic acid.

6. The composition of claim 1, comprising, by weight:
5–75% of said at least one alkali metal alkylarylsulfonate; and
25–70% of said hydroperoxide.

7. The composition of claim 6, wherein said at least one alkali metal alkylarylsulfonate is the sodium salt of p-cumene sulfonic acid, cymene sulfonic acid or diisopropylbenzene sulfonic acid.

8. The composition of claim 1, wherein said alkali metal M is sodium.

9. The composition of claim 1, wherein n is 0 or 1.

10. The composition of claim 1, wherein R' is methyl or isopropyl.

11. A dry detergent composition containing up to 30% of a solid, dry bleaching agent comprising (a) at least one alkali metal alkylarylsulfonate having the formula:

wherein
M is an alkali metal;
R' is lower alkyl; and
n is 0, 1, 2, 3, or 4; and
(b) the hydroperoxide obtained by hydroperoxidation of said at least one alkali metal alkylarylsulfonate and having the formula wherein M, R' and n are as defined above;
wherein the amount of said hydroperoxide contained in said detergent composition is from 0.1 to 21% by weight of said detergent composition.

12. The detergent composition of claim 11, which further comprises sodium perborate.

13. The detergent composition of claim 12, wherein the amount of sodium perborate is up to 5% by weight and the amount of said hydroperoxide contained in said detergent composition is from 2 to 4% by weight.

14. The detergent composition of claim 11, further comprising at least one anionic detergent, at least one soap, at least one non ionic detergent, sodium tripolyphosphate, sodium silicate and at least one of sodium sulfate or sodium carbonate.

15. The detergent composition of claim 11, containing up to 1000 ppm by weight copper as a water soluble cupric salt.

16. The detergent composition of claim 15, containing up to 5% of at least one copper complexing agent, said complexing agent being nitrilotriacetic acid, ethylenediaminetetracetic acid, their alkali metal salts, or mixtures thereof.

17. The detergent composition of claim 11, containing a base in an amount sufficient to bring the pH of the aqueous solutions of said composition to a value between 9 and 12.

18. The detergent composition of claim 14, wherein said hydroperoxide is one of sodium isopropylbenzene sulfonate hydroperoxide and sodium diisopropylbenzene sulfonate monohydroperoxide.

19. The detergent composition of claim 11, wherein said bleaching agent further comprises the alcohol resulting from the partial decomposition of said hydroperoxide and having the formula wherein M, R' and n are as defined in claim 11.

20. The detergent composition of claim 19, wherein the amount of said alcohol is up to 30% by weight of said bleaching agent.

21. The dry detergent composition of claim 19, wherein said bleaching agent comprises:
- 5-75% by weight of said at least one alkali metal alkylarylsulfonate;
- 25-70% by weight of said hydroperoxide; and up to 30% by weight of said alcohol.

22. The detergent composition of claim 11, wherein said bleaching agent comprises:
- 5-75% by weight of said at least one alkali metal alkylarylsulfonate; and
- 25-70% by weight of said hydroperoxide.

23. The detergent composition of claim 11, wherein the amount of said hydroperoxide contained in said detergent composition is from 0.1 to 5% by weight of said detergent composition.

24. A process for producing a solid, dry composition suitable for use as a bleaching agent in detergents and comprising:
(a) at least one alkali metal alkylarylsulfonate having the formula:

wherein
M is an alkali metal;
R' is lower alkyl; and
n is 0, 1, 2, 3, or 4; and
(b) the hydroperoxide obtained by hydroperoxidation of said at least one alkali metal alkylarylsulfonate and having the formula:

wherein M, R' and n are as defined above;
said process comprising the steps of:
(1) contacting an aqueous solution of said sulfonate with oxygen, at a temperature not higher than 85° C., at a pH between 9 and 10.5, in the presence as catalyst of 1-50 ppm, with respect to the alkylarylsulfonate, of cobalt as cobalt naphthenate; the reaction being continued until up to about 50% of said alkali metal alkylarylsulfonate has reacted, to form a resultant solution containing unreacted alkylarylsulfonate and its hydroperoxide;
(2) partially crystallizing said resultant solution and separating the resultant crystals from the supernatant, whereby the supernatant is enriched in hydroperoxide; and
(3) evaporating said supernatant to dryness under vacuum at a temperature of up to 40° C. to produce said solid, dry composition.

25. The process of claim 24, wherein the hydroperoxidation reaction is continued until a dry sample obtained by vacuum drying an aliquot of the solution contains at least about 25% hydroperoxide.

26. The process of claim 24, wherein the hydroperoxidation reaction is effected in the presence of a peroxide.

27. The process of claim 9, wherein the hydroperoxidation reaction is effected in the presence of 5-10 parts by weight of pure hydrogen peroxide for 100 parts by weight of said alkylarylsulfonate.

28. The process of claim 9, wherein said peroxide is the hydroperoxide of an alkali metal alkylarylsulfonate having the formula:

wherein M is an alkali metal; R is lower alkyl; and n is 0, 1, 2, 3 or 4.

29. The process of claim 24, wherein said partial crystallization is effected by cooling said resultant solution to 0°-20° C.

30. The process of claim 24, wherein said partial crystallization is effected by concentrating said resultant solution under vacuum at a maximum temperature of 40° C., and cooling the resultant concentrated solution to a temperature between 0° and 20° C.

31. The process of claim 24, wherein said partial crystallization is effected by dry concentrating said resultant solution under vacuum, taking up the resultant product in methanol, and cooling the resultant methanolic suspension to about 5° C.

32. The process of claim 24, wherein the peroxidation reaction is effected at a pH between 9.5 and 10.

33. The process of claim 24, wherein step (2) further comprises subjecting said supernatant to at least one cycle of concentrating said supernatant, effecting a partial crystallization of the resultant concentrated supernatant, and separating the resultant crop of crystals from the concentrated supernatant, which is thereby further enriched in hydroperoxide.

34. A process for increasing the relative proportion of hydroperoxide in an aqueous solution containing an alkali metal alkylarylsulfonate and the corresponding hydroperoxide, which comprises the step of effecting a partial crystallization of said solution and separating the resultant crystals from the supernatant, whereby the supernatant is enriched in hydroperoxide and the crystals are largely unreacted alkylarylsulfonate; wherein said alkali metal alkylarylsulfonate has the formula wherein M is an alkali metal; R' is lower alkyl; and n is 0, 1, 2, 3 or 4.

35. A solid, dry composition suitable for use as a bleaching agent in detergents, comprising:
(a) at least one alkali metal alkylarylsulfonate having the formula:

wherein:
M is an alkali metal;
R' is lower alkyl; and
n is 0, 1, 2, 3 or 4; and
(b) the hydroperoxide obtained by hydroperoxidation of said at least one alkali metal alkylarylsulfonate and having the formula wherein M, R' and n are as defined above;
wherein said composition is produced by the process of claim 24.

36. A dry detergent composition containing up to 30% of a solid, dry bleaching agent comprising:
(a) at least one alkali metal alkylarylsulfonate having the formula:

wherein:
M is an alkali metal;
R' is lower alkyl; and
n is 0, 1, 2, 3, or 4; and
(b) the hydroperoxide obtained by hydroperoxidation of said at least one alkali metal alkylarylsulfonate and having the formula wherein M, R' and n are as defined above;
wherein the amount of said hydroperoxide contained in said detergent composition is from 0.1 to 21% by weight of said detergent composition; and
wherein said bleaching agent is a composition produced by the process of claim 24.

* * * * *